United States Patent [19]

Hanes et al.

[11] Patent Number: 6,150,591
[45] Date of Patent: Nov. 21, 2000

[54] DOUBLE FLOWER GENE OF VERBENA AND THE METHOD OF PRODUCING SAME

[75] Inventors: Mitchell Eugene Hanes, Morgan Hill; Stanislaw Nalepa, Salinas, both of Calif.

[73] Assignee: Goldsmith Seeds, Inc., Gilroy, Calif.

[21] Appl. No.: 09/165,363

[22] Filed: Oct. 2, 1998

[51] Int. Cl.⁷ .............................. A01H 5/10; A01H 5/00; A01H 1/04; A01H 4/00; C12N 5/04

[52] U.S. Cl. ..................... 800/323; 800/298; 800/260; 800/276; 435/410

[58] Field of Search ................................. 800/323, 298, 800/260, 276; Plt./308; 435/410

[56] References Cited

U.S. PATENT DOCUMENTS 5,744,693  4/1998  Meyerowitz et al. .................. 800/205

OTHER PUBLICATIONS

Drews et al. Genetic control of flower development, Trends in Genetics, vol. 5, No. 8, pp. 256–261, 1989.

Lonnig et al. The homeotic Macho mutant of Antirrhinum majus reverts to wild–type or mutates to the homeotic plena phenotype, Molecular and general Genetics, vol.. 245, pp. 636–643, 1994.

van der Krol et al. Flower development in Petunia, The Plant Cell, vol. 5, pp. 1195–1203, 1993.

*Primary Examiner*—Elizabeth F. McElwain
*Assistant Examiner*—Melissa L. Kimball
*Attorney, Agent, or Firm*—Rothwell, Figg, Ernst & Kurz

[57] ABSTRACT

The present invention relates to a novel double flower gene in Verbena which is phenotypically expressed in the formation of flowers with one or more additional petals than existing Verbena cultivars. The present invention also relates to a Verbena seed, a Verbena plant, a Verbena flower, a Verbena variety and a Verbena hybrid which comprise the novel double flower gene. The present invention also relates to a method of producing the disclosed Verbena plants and seeds.

12 Claims, No Drawings

DOUBLE FLOWER GENE OF VERBENA AND THE METHOD OF PRODUCING SAME

BACKGROUND OF THE INVENTION

The present invention relates to a novel double flower gene in Verbena. The present invention also relates to a Verbena seed, a Verbena plant, Verbena flower, a Verbena variety and a Verbena hybrid which comprise the novel double flower gene.

Verbena belongs to the family Verbaceae. Verbena is a popular garden plant that can be used in beds, pots and baskets. It is generally sold as a spring annual in cell packs, although it can be grown as a tender perennial in mild climate regions. Verbena is commercially grown from either seed or cuttings. The varieties, usually grown from seed, are sold in cell packs and are generally more compact and less trailing than the vegetatively propagated varieties. Vegetative lines are frequently sold in larger pots as a specimen plant, and are also used as trailing plants for the garden and for hanging baskets. Within the last few years, plant breeding companies have introduced many new vegetative lines and the potential market for these is significant and expanding. Verbena is valued for its tolerance to direct sunlight, its ease of cultivation and a wide range of flower colors.

With existing cultivars, the Verbena flower has five petals. To date, there have been no double flowered Verbena plants reported in the relevant literature. Other flower crops that have double flower forms include Aster (*Callistephus sinensis*), African Marigold (*Tagetes erecta*), Stock (*Matthiola incana*), Nasturtium (*Tiopaecolum majus*), petunia, impatiens, geranium and carnation. Double flower plants typically have relatively little seed set and therefore flower more continuously with less of a tendency to cycle in and out of flower throughout the growing season. This attribute is valued especially in vegetatively propagated varieties. A double flowered Verbena variety, if available, would be particularly desirable for use as trailing plants for the garden and for hanging baskets.

SUMMARY OF THE INVENTION

The present invention relates to a novel double flower gene in Verbena which is phenotypically expressed in the formation of flowers with few to many more petals than existing Verbena cultivars. The present invention also relates to a Verbena seed, a Verbena plant, a Verbena flower, a Verbena variety and a Verbena hybrid which comprise the novel double flower gene. The present invention also relates to a method of producing the disclosed Verbena plants and seeds.

The gene involved has been determined to be a single, recessive gene based on the segregation ratio when single flower plants, heterozygous for the double flower gene, were self seeded. The double flower gene has been readily crossed into breeding lines and double flower plants of every color class have been produced. Thus, the gene is not linked to genes for color and is not deleterious to the plant.

DETAILED DESCRIPTION OF THE INVENTION

The present invention relates to a novel double flower gene in the genus Verbena which is phenotypically expressed in the formation of flowers having one or more additional petals versus existing Verbena cultivars which have five petals. The present invention also relates to a Verbena seed, a Verbena plant, a Verbena flower, a Verbena variety and a Verbena hybrid which comprise the novel double flower gene. The present invention also relates to a method of producing the disclosed Verbena plants and seeds.

The gene involved has been determined to be a single, recessive allele based on the segregation ratio when single flower plants, heterozygous for the double flower gene, were self seeded. The double flower allele has been readily crossed into breeding lines and double flower plants of every color class have been produced. Thus, it appears that the allele is not linked to other genes for color and is not deleterious to the plant.

The Verbena of the present invention was an unexpected result that arose from a Verbena mutation breeding project. A Verbena breeding line, known as 2005-2A, was used in an induced mutation project for the purpose of enhancing seed germination. Line 2005-2A is an inbred line that is true breeding for plant habit, flower color and single flower form.

After a series of preliminary dosage tests, the Verbena seeds were treated with the chemical mutagen, nitrosomethyl urea (NMU). After six hours of exposure to NMU, the seeds were sown under controlled conditions in a greenhouse and subsequently transplanted to a field plot.

In the first generation, $M_1$ generation, the seedlings exhibited typical symptoms of mutation treatment such as yellow flashing on the leaves and stunted abnormal growth of the plants. All plants in the $M_1$ generation were of single flower form. Seed was gathered from those $M_1$ generation plants having the most visible phenotypic indication of mutation. The bulk seeds were sown in the greenhouse in Gilroy, California in September, 1994 under the sowing number of Mu45. Plants appeared in the $M_2$ generation that had a double flower form. This mutation has never been observed in this line, or any other Verbena line, prior to the $M_2$ generation of this mutation breeding project.

The double flower $M_2$ generation plants were outcrossed to known single flower lines. The resulting $F_1$ hybrid plants exhibited 100% single flower form suggesting that the double flower form is a recessive trait. Selfed $F_1$ plants that were heterozygous for the double flower allele and phenotypically single flower yielded a population that segregated ¼ double flower phenotypes and ¾ single flower phenotypes. The segregation of double flower plants in this ratio confirms that the double flower trait is controlled by a single recessive gene.

The double flowered Verbena mutant of the present invention was crossed into other seed lines and into vegetative lines. A series of Verbena plants, in every color class and expressing the double flower trait in the $F_2$ generation, was produced. This indicates the gene is not linked to color genes and does not carry a deleterious genetic load. Self seed from this series of plants yielded plants which were all double flowered. The flower forms ranged from forms with a complete second complement of petals to forms with a single extra petal. Expression of the double flower gene appears to be influenced by the environmental conditions under which the plant is grown, with stress reducing the degree of the double flower trait. This stress effect is also seen with other double flower crops, such as geraniums and impatiens.

The Verbena plants of the present invention have reduced pollen yields which result in a significant reduction in seed production of naturally pollinated plants, as compared to intentional hand pollination plants. This provides a great benefit because it results in continued flowering and reduced occurrence of undesirable seed heads which must be removed to maintain an attractive plant specimen. Additionally the elimination of biological load, due to the reduction in seed set, means the Verbena of the present invention is less susceptible to plant diseases such as powdery mildew.

In order to provide an understanding of several of the terms used in the specification and claims, the following definitions are provided:

"Double flower" refers to the presence of more than the native complement of petals. In the case of Verbena, this means more than five (5) petals.

The term "plant" includes plant cells, plant protoplasts, plant cells of tissue culture from which Verbena plants can be regenerated, plant calli, plant clumps and plant cells that are intact in plants or parts of plants such as pollen, flowers, seed, leaves, stems and the like.

EXAMPLES

The present invention is further detailed in the following Examples, which are offered by way of illustration and are not intended to limit the invention in any manner. Standard techniques well known in the art or the techniques specifically described are utilized.

Example 1

Chemical Mutagen Treatment of Verbena

A Verbena breeding line known as 2005-2A was used for the induced mutation project. Line 2005-2A is an inbred line that is true breeding for plant habit, flower color and single flower form. Dry seeds were submerged for 24 hours in distilled water to complete saturation and kept moist in petri dishes for 24 hours to ensure oxygen was available for metabolic activity. The seeds were then split into two groups and each group was exposed to fresh aqueous solutions of either 0.03% NMU or 0.09% NMU for six hours each at 20–22 degrees C. The seeds were rinsed for 30 minutes and immediately sown in the greenhouse and subsequently transplanted to a field plot. In the first generation after treatment, the $M_1$ generation, the two treatment population totaling approximately 1,500 seedlings exhibited typical symptoms of mutation treatment such as yellow flashing on the leaves and stunted, abnormal plant growth. All $M_1$ generation plants had flowers that were red with a white throat and single flower form. Seed was bulked from those plants with the most visible phenotypic indication of mutation. Bulk seed was sown in the greenhouse in Gilroy, California in September, 1994 under the sowing number of Mu45. Plants appeared in the $M_2$ generation that had double flower form. This trait had not been observed in this line, or any other Verbena line, prior to the $M_2$ generation of this mutation breeding project.

Example 2

Lack of Double Flower Trait in Existing Verbena Cultivars and Wild Verbena spp.

No double flower Verbena has been reported in the relevant literature. Double flower Verbena have not been observed by Goldsmith Seeds, Inc. in the extensive breeding and testing of commercial material or recombinations of breeding lines, except for the present invention.

Example 3

Genetic Segregation of Double Flower Trait in $F_2$ Hybrid Cultivars

The double flower, $M_2$ generation plants were outcrossed to known true breeding, single flower lines. The double flower "female" line, manually emasculated, was pollinated with pollen from the single flower ("male") line. The resulting $F_1$ hybrid plants were all single flower form, suggesting that the double flower form is a recessive trait. Selfed $F_1$ generation plants, which were heterozygous for the double flower gene and phenotypically single flower, yielded an $F_2$ population that segregated ¼ double flower phenotypes and ¾ single flower phenotypes. Selfed seed from these double flowered, $F_2$ generation plants yielded 100% double flower plants. These results confirm that the double flower trait is controlled by a single recessive gene. The degree of the double flower trait ranged, from forms with a complete second complement of petals to forms with a single additional petal.

Expression of the double flower gene appears to be influenced by the environmental conditions under which the plant is grown, with stress reducing the degree of double flower trait. This stress effect is also seen with other double flower crops, such as geranium and impatiens.

Example 4

Additional Benefits of Double Flower Form

The Verbena plants of the present invention have reduced pollen yields which result in a significant reduction in seed production of naturally pollinated plants as compared to intentional hand pollinated plants. This provides a great benefit because it results in continued flowering and reduced occurrence of undesirable seed heads which must be removed to maintain an attractive plant specimen. Additionally, the elimination of biological load, due to the reduction in seed set, means the Verbena of the present invention is less susceptible to plant diseases such as powdery mildew.

Example 5

Cross Breeding the Double Flower Trait into Verbena Cultivars

The double flowered Verbena mutant of the present invention was crossed into other seed lines and into vegetative lines. A series of Verbena plants, in every color class and expressing the double flower trait in the $F_2$ generation, was produced. This indicates that the gene is not linked to color genes and does not carry a deleterious genetic load. Self seed from this series of plants yielded plants which were all double flowered.

Examples:

a) Mu45-11, a red double flowered plant was crossed to 130-2 blue single flowered plant. The resulting seed was sown under the population number Mu223 and all of the progeny was of the single flower phenotype.

b) A red single flowered plant, Mu223-5 was selected and when self pollinated seed was produced on this plant, double flowered plants were obtained in the next generation. These double flowered plants had flower colors of burgundy and blue. The burgundy plant is identified as plant Mu275-1 and the blue plants are known by the designations Mu275-2, Mu275-3 and Mu275-4.

c) A second plant, known as Mu223-3, that also had a red single flower was selected and self pollinated. The seed of this pollination yielded plants that extended the color range of double flowered types to deep rose (Mu273-2).

DEPOSIT INFORMATION

Verbena seeds containing a double flower gene have been placed on deposit with the American Type Culture Collection (ATCC), Manassas, Va. 20110-2209, under Deposit Accession Number 203298 on Sep. 29, 1998.

Although the foregoing invention has been described in some detail by way of illustration and example for purposes of clarity and understanding, it will be obvious that certain changes and modifications may be practiced within the scope of the invention, as limited only by the scope of the appended claims.

What is claimed is:

1. A Verbena seed containing a double flower gene, wherein said seed is deposited under ATCC designation No. 203298.

2. The Verbena seed of claim 1, wherein said seed contains a recessive allele for double flower.

3. A Verbena plant produced by growing the seed of claim 1.

4. Pollen of the plant of claim 3.

5. An ovule of the plant of claim 3.

6. A tissue culture comprising regenerable cells of the plant of claim 3.

7. A method for producing $F_1$ hybrid Verbena seed comprising crossing a first parent Verbena plant with a second parent Verbena plant and harvesting the resultant $F_1$ hybrid Verbena seed, wherein said first or second Verbena plant is the Verbena plant of claim 3.

8. A first generation ($F_1$) Verbena plant, or parts thereof, produced by growing said hybrid Verbena seed of claim 7.

9. Seed produced from the $F_1$ plant of claim 8.

10. The Verbena plant of claim 3, wherein said double flower has more than five petals.

11. The Verbena plant of claim 3, wherein said double flower has six to ten petals.

12. Verbena seeds and plants grown from the Verbena seeds containing a double flower gene, wherein said seed is deposited under ATCC accession No. 203298, and succeeding generations thereof to which said double flower gene is transferred.

* * * * *